United States Patent
Park et al.

(10) Patent No.: US 10,349,949 B2
(45) Date of Patent: Jul. 16, 2019

(54) CLOSED LOOP-TYPE HEMOSTATIC CLIPPING DEVICE HAVING BUILT-IN INNER PINCERS

(71) Applicant: NATIONAL CANCER CENTER, Gyeonggi-do (KR)

(72) Inventors: Sang Jae Park, Gyeonggi-do (KR); Kwang Gi Kim, Seoul (KR); Seong Yeon Cho, Gyeonggi-do (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 79 days.

(21) Appl. No.: 15/101,403

(22) PCT Filed: Dec. 2, 2014

(86) PCT No.: PCT/KR2014/011658
§ 371 (c)(1),
(2) Date: Jun. 2, 2016

(87) PCT Pub. No.: WO2015/084009
PCT Pub. Date: Jun. 11, 2015

(65) Prior Publication Data
US 2016/0302795 A1     Oct. 20, 2016

(30) Foreign Application Priority Data

Dec. 2, 2013   (KR) .................... 10-2013-0148766

(51) Int. Cl.
*A61B 17/128*   (2006.01)
*A61B 17/122*   (2006.01)
A61B 17/00     (2006.01)

(52) U.S. Cl.
CPC ........ *A61B 17/1285* (2013.01); *A61B 17/122* (2013.01); *A61B 2017/00367* (2013.01)

(58) Field of Classification Search
CPC ... A61B 17/128; A61B 17/12; A61B 17/1285; A61B 17/122; A61B 2017/00367
See application file for complete search history.

(56) References Cited

U.S. PATENT DOCUMENTS 6,139,555 A  * 10/2000  Hart ................... A61B 17/1285
                                                          606/139
6,551,315 B2    4/2003  Kortenbach et al.
(Continued)

OTHER PUBLICATIONS

Notice of Allowance dated Apr. 1, 2015 issued by Korean Patent Office in Korean Patent Application No. 10-2013-0148766, which is the corresponding Korean Patent Application to the present application, and the base application to which the present application claims priority to.

*Primary Examiner* — Thomas M McEvoy
(74) *Attorney, Agent, or Firm* — Porzio Bromberg & Newman P.C.

(57) ABSTRACT

A closed loop-type hemostatic device having built-in inner pincers which integrates holding type pincers with a device for fitting a hemostatic clip, so as to: primarily, find and temporarily perform hemostasis on a bleeding portion by using holding type pincers after confirming that the bleeding portion exists; secondarily, move a clip pressing part and a clip pressing part and enclose the bleeding portion; and then move only the clip pressing part and clip a closed loop-type hemostatic clip onto the bleeding portion so as to perform hemostasis. The amount of bleeding can be reduced by temporary hemostasis on a bleeding portion, and a hemostatic clip can be precisely clipped on the bleeding portion, thereby improving hemostatic performance. Also, because hemostasis can be selectively performed only around a damaged blood vessel wall, therefore, the physiological benefit of being able to maintain partial blood flow may be provided.

3 Claims, 5 Drawing Sheets

(56) References Cited

U.S. PATENT DOCUMENTS

| | | |
|---|---|---|
| 6,569,085 B2 | 5/2003 | Kortenbach et al. |
| 6,716,226 B2 | 4/2004 | Sixto, Jr. et al. |
| 6,743,240 B2 | 6/2004 | Smith et al. |
| 6,824,548 B2 | 11/2004 | Smith et al. |
| 6,843,794 B2 | 1/2005 | Sixto, Jr. et al. |
| 6,945,979 B2 | 9/2005 | Kortenbach et al. |
| 7,019,518 B2 | 3/2006 | Amini et al. |
| 7,070,602 B2 | 7/2006 | Smith et al. |
| 7,083,617 B2 | 8/2006 | Kortenbach et al. |
| 7,083,618 B2 | 8/2006 | Couture et al. |
| 7,090,673 B2 | 8/2006 | Dycus et al. |
| 7,090,685 B2 | 8/2006 | Kortenbach et al. |
| 7,101,371 B2 | 9/2006 | Dycus et al. |
| 7,101,372 B2 | 9/2006 | Dycus et al. |
| 7,131,971 B2 | 11/2006 | Dycus et al. |
| 7,232,445 B2 | 6/2007 | Kortenbach et al. |
| 7,255,697 B2 | 8/2007 | Dycus et al. |
| 7,357,806 B2 | 4/2008 | Rivera et al. |
| 7,384,420 B2 | 6/2008 | Dycus et al. |
| 7,615,058 B2 | 11/2009 | Sixto, Jr. et al. |
| 7,727,246 B2 | 6/2010 | Sixto, Jr. et al. |
| 7,727,248 B2 | 6/2010 | Smith et al. |
| 7,828,811 B2 | 11/2010 | Kortenbach et al. |
| 7,942,885 B2 | 5/2011 | Sixto, Jr. et al. |
| 8,021,378 B2 | 9/2011 | Sixto, Jr. et al. |
| 8,062,314 B2 | 11/2011 | Sixto, Jr. et al. |
| 8,066,721 B2 | 11/2011 | Kortenbach et al. |
| 2002/0043973 A1 | 4/2002 | Amini et al. |
| 2002/0068935 A1 | 6/2002 | Kortenbach et al. |
| 2002/0068945 A1 | 6/2002 | Sixto, Jr. et al. |
| 2002/0078967 A1 | 6/2002 | Sixto, Jr. et al. |
| 2002/0138086 A1 | 9/2002 | Sixto, Jr. et al. |
| 2002/0188294 A1 | 12/2002 | Couture et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2002/0198549 A1 | 12/2002 | Sixto, Jr. et al. |
| 2003/0018331 A1 | 1/2003 | Dycus et al. |
| 2003/0036679 A1 | 2/2003 | Kortenbach et al. |
| 2003/0191478 A1 | 10/2003 | Kortenbach et al. |
| 2003/0195387 A1 | 10/2003 | Kortenbach et al. |
| 2003/0229344 A1 | 12/2003 | Dycus et al. |
| 2003/0233092 A1 | 12/2003 | Kortenbach et al. |
| 2004/0082952 A1 | 4/2004 | Dycus et al. |
| 2004/0116948 A1 | 6/2004 | Sixto, Jr. et al. |
| 2004/0193186 A1 | 9/2004 | Kortenbach et al. |
| 2004/0243125 A1 | 12/2004 | Dycus et al. |
| 2004/0249371 A1 | 12/2004 | Dycus et al. |
| 2005/0033333 A1 | 2/2005 | Smith et al. |
| 2005/0049616 A1 | 3/2005 | Rivera et al. |
| 2005/0090837 A1 | 4/2005 | Sixto, Jr. et al. |
| 2005/0090838 A1 | 4/2005 | Sixto, Jr. et al. |
| 2005/0125010 A1 | 6/2005 | Smith et al. |
| 2005/0149017 A1 | 7/2005 | Dycus |
| 2006/0189981 A1 | 8/2006 | Dycus et al. |
| 2007/0027458 A1 | 2/2007 | Sixto, Jr. et al. |
| 2007/0055231 A1 | 3/2007 | Dycus et al. |
| 2007/0062017 A1 | 3/2007 | Dycus et al. |
| 2007/0142851 A1 | 6/2007 | Sixto, Jr. et al. |
| 2007/0260242 A1 | 11/2007 | Dycus et al. |
| 2007/0265640 A1 | 11/2007 | Kortenbach et al. |
| 2008/0051808 A1 | 2/2008 | Rivera et al. |
| 2008/0207995 A1 | 8/2008 | Kortenbach et al. |
| 2009/0292282 A9 | 11/2009 | Dycus |
| 2011/0066163 A1 | 3/2011 | Cho et al. |
| 2011/0071547 A1 | 3/2011 | McBrayer et al. |
| 2011/0071554 A1 | 3/2011 | McBrayer et al. |
| 2011/0071555 A1 | 3/2011 | McBrayer et al. |
| 2011/0125168 A1 | 5/2011 | Sixto, Jr. et al. |

\* cited by examiner

200

CLOSED LOOP-TYPE HEMOSTATIC CLIPPING DEVICE HAVING BUILT-IN INNER PINCERS

BACKGROUND OF THE INVENTION

Field

The present disclosure relates to a hemostatic device thereof, and more particularly, to a closed loop-type hemostatic clipping device having built-in inner pincers which applies pressure to bleeding portion using pincers for primary hemostasis, and then applies secondary pressure to the hemostatic location by clipping using the closed loop-type hemostatic clipping device.

Description of the Related Art

The procedure of amputating a vein or artery or controlling hemorrhage frequently occurs in various surgical operations, particularly in organ resection.

Particularly, bleeding may occur in medium or large caliber blood vessels in the case of amputation of blood vessels or mistakes and accidents while performing laparotomy and laparoscope operation.

Since the blood vessel may lead to serious problems when the hemorrhage is caused by minute damage, therefore, it is needed to pay particular attention.

Therefore, various ways have been sought to control hemorrhage on the bleeding portion.

Recent methods of performing hemostasis are hemostatic clipping and using a clip installation device having a hemostatic clip.

An example of this is disclosed in U.S. Pat. No. 7,090,685 (hereafter in this specification referred to as 'Related Art Document'.)

In the related art document, each hemostatic clip presses opposite sides of the bleeding portion and occludes the whole blood vessel.

However, as described above, the method of performing hemostasis in the related art document has a problem in prolonged hemostasis time because such opposite sides of the bleeding portion should be pressed by each hemostatic clip An operation may have difficulty due to occurring excessive bleeding when the hemostasis time is prolonged.

In addition, it brings to a physiologically adverse result because an impaired blood vessel may be occluded and block the bloodstream.

A conventional hemostatic clip which is a bent I-shaped metal into a U-shaped metal is used mostly.

However, the U-shaped clip is subject to restriction in a range of use.

That is, when the blood vessel is inserted in a blood system and a cross-sectional end is protruded, or the blood vessel is occluded partially rather than occluded completely, it is difficult to apply.

Further, seeking the bleeding portion inaccurately may occur because leaked blood may obstruct securing a clear view regarding the bleeding portion, in this case, bleeding may keep occurring even though clipping the hemostatic clip is clipped by speculating a suspicious bleeding portion.

Then, an increase of operation time and a patient safety issue may occur because an operator has to remove the clipping hemostatic clip in the blood vessel and seek the bleeding portion again to be clipped.

Also, in the related art, the hemostasis is performed temporarily using operating forceps on the bleeding portion, however, in the case of the complete hemostasis, removing the operating forceps and moving the clipping installation device into the bleeding portion had to be carried out.

In such a case, the installation device should clip by aiming at the bleeding portion accurately, however, aiming at the bleeding portion accurately was difficult in the process of removing the operating forceps and aiming the clipping device.

Accordingly, continuous bleeding may occur because of an inaccurate performing hemostasis on the bleeding portion.

DETAILED DESCRIPTION OF THE INVENTION

Technical Problem

Therefore, the present disclosure provides a closed loop-type hemostatic clipping device having built-in inner pincers that can temporarily perform hemostatic by seeking the bleeding location accurately, and then it is capable of applying two-step pressure hemostasis to the bleeding portion by clipping the bleeding portion accurately.

Also, the present disclosure provides a shaped closed loop-type hemostatic clipping device, which supplements the weakness of a U shaped conventional hemostatic clip, that can not only complete occlusion of the impaired blood vessel but allows occlusion confining the impaired blood vessel, therefore, it allows performing hemostatic by remaining the bloodstream partially.

In other words, the present disclosure provides a two-step pressure hemostasis device to the bleeding portion which has a shaped closed loop-type hemostatic clip and a clipping installation device that installs on the blood vessel.

Solution to Problem

In an aspect of the present disclosure, the present disclosure provides a first trigger and second trigger on a body; holding type pincers that hold a bleeding portion according to control of the first trigger; a clip holding part that moves to the bleeding portion according to control of the second trigger. The closed loop-type hemostatic clipping device having built-in inner pincers including a hemostatic clip that clips the bleeding part contained within the clip holding part according to the clip pressing part operation in a contained state.

A trigger stopper operates only the second trigger when the holding type pincers operate according to the control of the first trigger.

The clip holding part moves in company with the clip pressing part in an initial section and the clip pressing part moves when the clip holding part reaches the holding type pincers.

A clip pressing part stopper moves only the clip pressing part and limits the moving of the clip holding part.

The clip holding part is composed of upper/lower clip holding part and a prevention sill for preventing separation of the hemostatic clip is formed at least one front clip holding part of the upper/lower clip holding part.

The hemostatic clip is a shaped closed loop-type hemostatic clip having an incision part at the center.

A width of the hemostatic clip incision part should be formed more widely than the width of the holding type pincers.

The present disclosure also provides that the pincers for holding temporarily perform hemostatic by holding the bleeding portion; the clip holding part covers the pincers for holding according to forward motion; the hemostatic clip is contained in the clip holding part; and the closed loop-type hemostatic clipping device having built-in inner pincers including the clip pressing part which clips the bleeding portion to occlude completely or occlude partially by pressing the clip holding part according to the forward motion.

Pressurization force of the clipping pressing part makes the hemostatic clip protrude from frontward to clip the bleeding portion.

Advantageous Effects of Invention

According to the closed loop-type hemostatic clipping device having built-in inner pincers thereof, it temporarily performs primary hemostatic using pincers after finding the bleeding portion, and covers the bleeding portion by moving the clip holding part and clip pressing part secondarily, and then performs hemostatic by moving the clip pressing part and clipping the hemostatic clip on the bleeding portion.

That is, the pincers for temporary hemostatic and the device for installing clip are formed integrally.

Therefore, the bleeding portion may be found accurately, the temporarily performing primary hemostatic using the holding type pincers may reduce the bleeding amount, and the hemostatic clip may clip accurately on the bleeding portion, therefore, hemostatic performance may have an improved effect.

Further, the hemostatic clip that clips on the bleeding portion is provided with a shaped closed loop-type hemostatic clip, it may be used for the complete occlude of the blood vessel and the partial occlude of blood vessel which is hard to apply the conventional U shaped clip to the medium or large caliber blood vessels, and may provide a physiological advantage that remains the bloodstream partially because of a selective hemostatic around the impaired blood vessel.

In addition, the hemostatic clip may be capable of installation easily at a different angle compared to the conventional U shaped clip, therefore, the stability may be increased in operation.

BEST MODES FOR CARRYING OUT THE INVENTION

Hereinafter, an exemplary embodiment of the present disclosure describes an example of the performing closed loop-type hemostatic clipping device having built-in inner pincers by referring to attached drawing.

Figure 1:
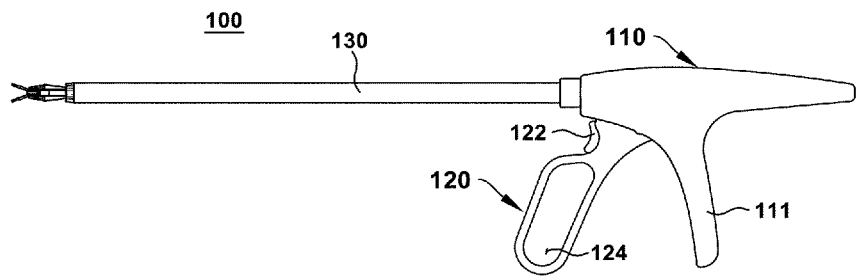
FIG. 1 is a block diagram illustrating a closed loop-type hemostatic clipping device which is capable of applying the two-step pressure hemostasis according to an exemplary embodiment of the present disclosure.
Figure 2:
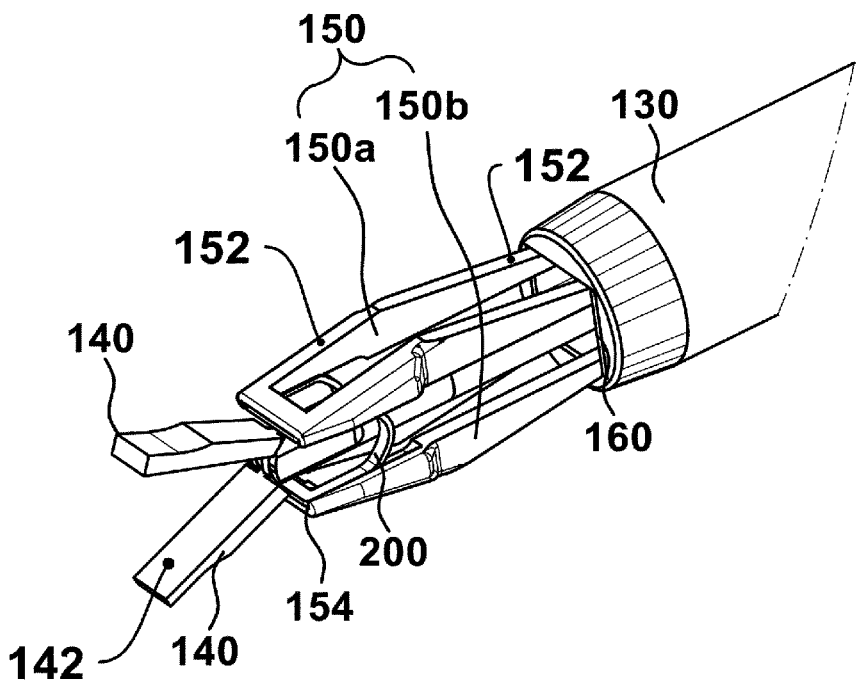
FIG. 2 shows a partial enlarged drawing that enlarged some composition of FIG. 1.
Figure 3:
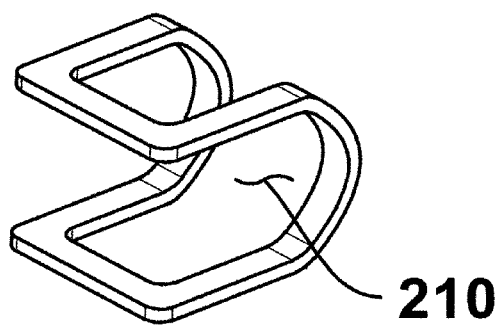
FIG. 3 shows a perspective view of the hemostatic clip illustrated in FIG. 2

FIG. 1 shows a drawing of the closed loop-type hemostatic clipping device having built-in inner pincers according to the exemplary embodiment of the present disclosure, FIG. 2 shows the partial enlarged drawing that enlarged some composition, and FIG. 3 shows the perspective view of the hemostatic clip shown in FIG. 2.

Referring to FIG. 1 and FIG. 2, the closed loop-type hemostatic clipping device having built-in inner pincers 100 is composed of body 110 with handle 111 which enables the operator holds in order to perform the temporary hemostatic regarding the bleeding portion and surgical operation action that clips the hemostatic clip on the bleeding portion.

The body 110 and the handle 111 are designed to hold and control conveniently.

That is, any shape for the body 110 and the handle 111 which the operator enables to operate with comfortable position during the operation time may be acceptable.

Trigger unit 120 is formed at the front side of the handle 111.

Trigger unit 120 contains the trigger having pincers 122 named the first trigger and the clipping trigger 124 named the second trigger which an operator controls using their own finger in order to enable performing temporarily hemostatic on the bleeding portion of the patient and performing clipping by pressing the hemostatic clip on the bleeding portion.

Even though, the drawing illustrates that forming of the trigger having pincers 122 on a part of the clipping trigger 124, it may not be necessary to form like the above.

In other words, even though location of the trigger having pincers 122 and the clipping trigger 124 are switched, it may be acceptable.

This means that it may be variously alterable according to convenience of the operator.

Trigger having pincers 122 provides performing temporarily hemostatic on the bleeding portion by operating the pincers for holding the bleeding portion.

Clipping trigger 124 provides a function that lets the hemostatic clip clips on the bleeding portion.

In regards to the trigger unit 120, it should be operated to operate the trigger having pincers 122 first, and then to operate the clipping trigger 124.

The bleeding portion is determined first through the primary hemostatic using the pincers for holding 140, and the bleeding portion is clipped using the hemostatic clip 200 when further bleeding has not occurred on the bleeding portion.

Effective hemostatic may not be performed when the clipping trigger 124 is operated in a state of finding the bleeding portion inaccurately by trying hemostatic using built-in pincers first, because the hemostatic clip, that is closed loop-type clip, may not cover the bleeding portion completely.

Therefore, the clipping trigger 124 should not be operated without operation of pincers for holding 140.

For this, although it is not illustrated in the drawing, the clipping trigger stopper is installed mechanically in order to the clipping trigger 124 is to be operated after the trigger having pincers 122 is operated inside the body 110.

In the case of the hemostatic clip, the clip holding part 150 and the clip pressing part 160 move together in the initial section pulling the clipping trigger 124, and the clip holding part 150 stops moving when it arrives at a certain location and then performs clipping by moving only the clip pressing part 160.

Therefore, the clip holding part 150 should be maintained at its determined location in a section of moving only the clip pressing part 160 even though the clip pressing part 160 is moved.

Clip holding part stopper (not illustrated) can be provided as an example above.

That is, when the clip holding part 150 arrives at the certain location, the clip holding part 150 stops moving because the clip holding part 150 reaches the clip holding part stopper.

Such composition is installed in the body 110.

A long-tube shaped shaft 130 is connected to one end of the body 110.

The shaft 130 has a length that enables the operator to operate the patient well in a state of holding the handle 111.

Further, various parts are installed inside of the shaft 130 in order to transfer mechanically a driving command of the trigger having pincers 122 and the clipping trigger 124.

That is, related devices are to be installed to close and open the pincers for holding 140 through the control of the trigger having pincers 122, and like the preceding, the related devices are to be installed to have the clip holding part 150 and the clip pressing part 160 moved through the control of the clipping trigger 124 in a connected state.

The pincers for holding 140 that is interlocked with the trigger having pincers 122, the clip holding part 150 and clip pressing part 160 that are interlocked with a pulling action of the clipping trigger 124 are composed in an end of the shaft 130.

In particular, the clip pressing part 160 is in an installed state before the clipping trigger 124 is pulled.

Further, the clip holding part 150 is in a state of being projected partially at the end of the shaft 130.

The clip holding part 150 is classified as upper/lower clip holding part 150a 150b and a part facing each other is formed flat, however, a reversed part is formed of a slope 152.

The slope 152 is being formed at both sides based on a middle of the upper/lower clip holding part 150a 150b.

A hemostatic clip 200 is contained inside of the clip holding part 150.

The hemostatic clip 200 has a function of clipping on the bleeding portion depending on the operation of the clip pressing part 160.

Therefore, the hemostatic clip 200 should be remained on the front of the upper/lower clip holding part 150a 150b to be installed safely.

Further, the hemostatic clip 200 should not be separated optionally from the upper/lower clip holding part 150a 150b before it is clipped.

In order to prevent the hemostatic clip 200 from separating, the prevention sill for preventing separation 154 may be formed on the front clip holding part of the upper/lower clip holding part 150a 150b.

The hemostatic clip 200 is illustrated in FIG. 3.

Referring to FIG. 3, the hemostatic clip 200 is to supplement the weakness of the conventional U shaped hemostatic clip.

That is, the hemostatic clip 200 of the exemplary embodiment of the present disclosure is used a closed loop-type hemostatic clip to perform hemostatic by remaining in the bloodstream partially.

When viewed from up and down direction in FIG. 3, it is formed into a shape with the incision part 210 formed at the center.

In addition, titanium is used for material of the hemostatic clip 200.

For example, titanium Grade 4 or titanium Grade 2 which has relatively low grade yield strength is used.

However, using other biocompatible material is possible.

Referring to FIG. 1 and FIG. 2 again, extended pincers for holding 140 is composed on the front clip holding part 150.

The pincers for holding 140 functions for performing temporary hemostatic on the bleeding portion by holding the bleeding portion.

Such a holding surface of pincers for holding 140 is formed into a flat surface, however, any shape for holding blood vessel may acceptable.

For example, the holding surface 142 is capable of being formed into a sawtooth shaped in order to improve friction force with the held blood vessel.

The pincers for holding 140 should not occur interference with the hemostatic clip 200.

The hemostatic clip 200 should be clipped by covering the bleeding portion in the state of performing temporary hemostatic on the bleeding portion with the pincers for holding 140.

At this time, the hemostatic clip 200 is needed to clip without crashing against the pincers for holding 140.

Thereby, the width of the hemostatic clip 140 should be formed within the width of the incision part 210.

MODES FOR CARRYING OUT THE INVENTION

Hereinafter, the process of applying secondary pressure on the bleeding portion using the closed loop-type hemostatic clipping device having built-in inner pincers having the above composition will be described with FIG. 4.

FIG. 4A to FIG. 4E are a state diagram of the closed loop-type hemostatic clipping device having built-in inner pincers.

First, when the bleeding occurs on the blood vessel 1, the bleeding portion A should be found.

The bleeding portion A should be found by the operator.

Figure 4A:
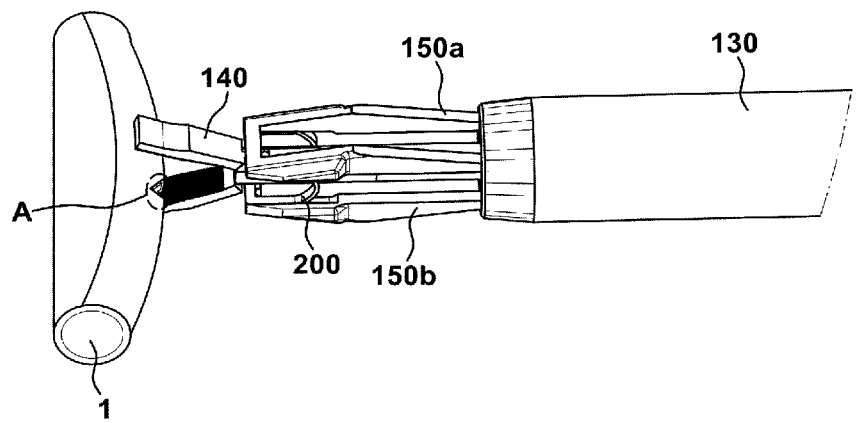
FIG. 4A to 4E show operational state drawing of the two step pressure hemostasis device

If there is suspicious bleeding area, the operator has to position the pincers for holding 140 on the bleeding portion A as illustrated in FIG. 4A.

In the state of such FIG. 4A, the operator pulls the trigger having pincers 122.

Then, the pincers for holding 140 connected with the trigger having pincers 122 structurally hold the bleeding portion A by closing.

Figure 4B:
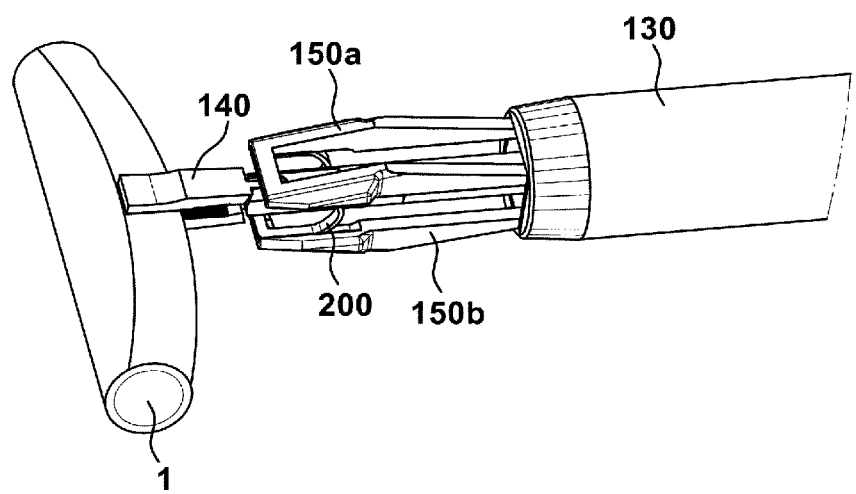

FIG. 4B illustrates the state of holding the bleeding portion A.

Accordingly, the pincers for holding 140 is capable of performing temporary hemostatic on the bleeding according to a holding operation.

However, if the bleeding does not stop even after a holding of the bleeding portion A with pincers for holding 140, the operator has to hold the bleeding portion by pulling the trigger having pincers 122 again after moving the pincers for holding 140 to another location.

Such work may proceed several times.

Consequently, if the bleeding has not occurred, designate that portion as a hemostatic portion.

Like the above, the operator is capable of finding the bleeding portion A through the process.

After finding the bleeding portion A accurately, pressure is applied to the hemostatic clip 200 after the hemostatic clip 200 is moved to the location of covering the bleeding portion.

In order to this, the operator pulls the clipping trigger 124.

Accordingly, in the initial section of pulling the clipping trigger 124, the clip holding part 150 is to be moved in company with the clip pressing part 160 until the clip holding part 150 reaches the location of covering holding type pincers 140.

The clip pressing part 160 has a shape which is coming from inside of the shaft 130.

Figure 4C:
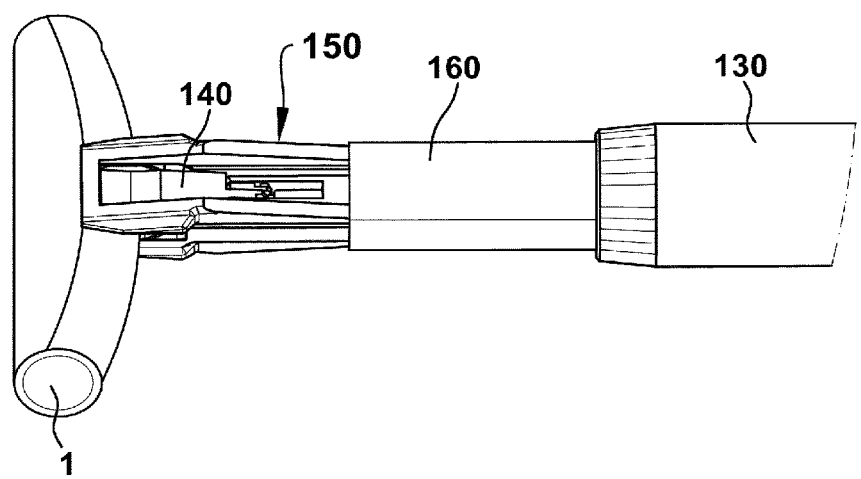

FIG. 4C illustrates this state.

Figure 4D:
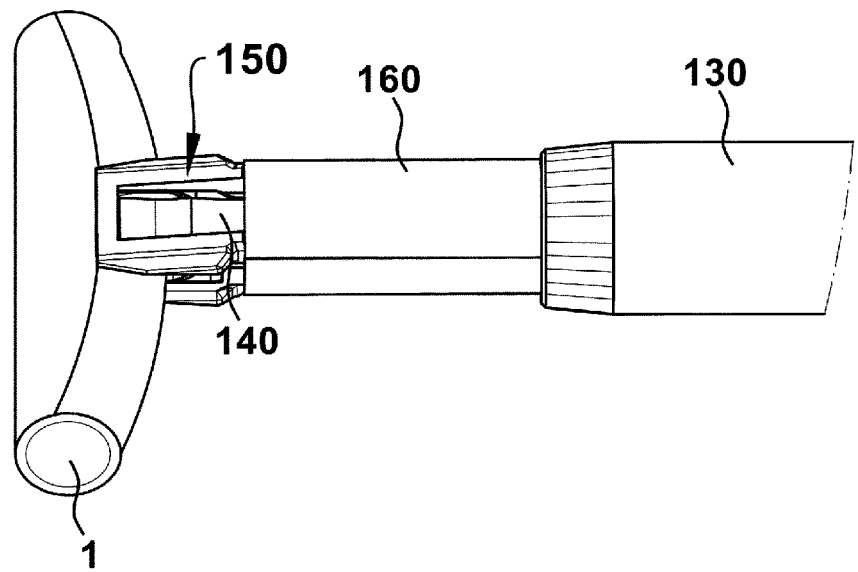

Further, the clip holding part 150 reaches the location of covering holding type pincers 140 as FIG. 4C, later, the clip holding part 150 stops moving in the state of pulling continually the clipping trigger 124 as illustrated in FIG. 4D and only the clip pressing part 160 is moved.

In particular, when the clip holding part 150 reaches the location of holding type pincers 140 performing temporary hemostatic on the bleeding portion, there is interference from the clip holding part stopper (not illustrated), therefore the clip holding part 150 stops moving and only the clip pressing part 160 moves continually.

That is, comparing to FIG. 4C and FIG. 4D, the clip pressing part 160 is in a better state in the shaft 130.

If only the clip pressing part 160 moves forward with a state of fixing the clip holding part 150, the clip pressing part 160 is pressed by the clip holding part 150 by moving in an up/down direction along the slope 152.

Hereupon, the hemostatic clip 200 installed in the clip holding part 150 protrudes to the front according to the clip pressing part 160 and is clipped by covering the bleeding portion.

Figure 4E:
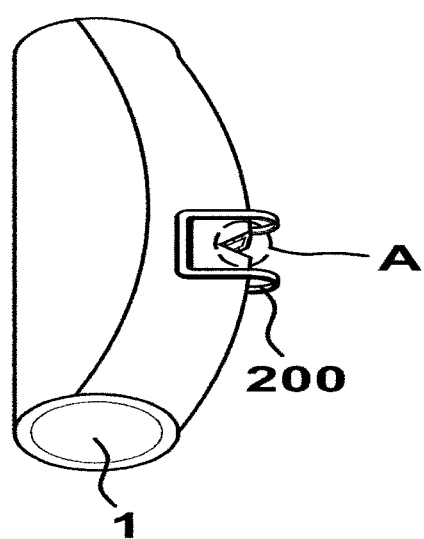

FIG. 4E illustrates a clipped state of the hemostatic clip 200 on the bleeding portion A.

Referring to FIG. 4E, the holding type pincers 140 that are used for temporary hemostatic is in the state of being removed.

Even though the holding type pincers 140 is removed, the bleeding portion A is performed hemostatic safely because the hemostatic clip 200 is clipped on an outer portion of bleeding portion A forming a closed loop.

That is, a part of a blood vessel is occluded partially rather than the blood vessel 1 being occluded completely, therefore, hemostatic by remaining bloodstream partially may be possible.

Such method of performing hemostasis may reduce bleeding blood significantly because of the primary performing temporary hemostatic, also, because hemostasis can be selectively performed on only the area around the damaged blood vessel wall, therefore, the physiological benefit of being able to maintain blood flow may be provided.

Figure 5:
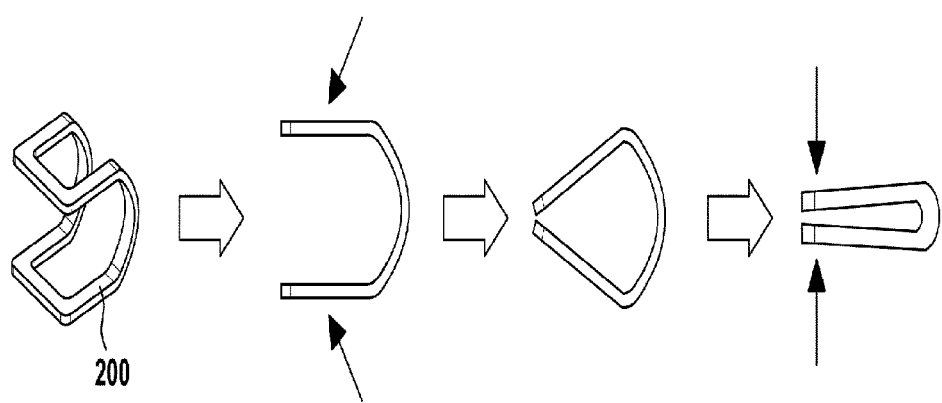
FIG. 5 illustrates a drawing of an exemplary that changes a shape of hemostasis clip according to pressure of the clip pressing part in an exemplary embodiment of the present disclosure

Meanwhile, FIG. 5 illustrates the example of the hemostasis clip 200 that changes shape according to moving of the clip pressing part 160.

Referring to FIG. 5, the hemostatic clip 200 is in an isolated state of facing an upper and lower part of the hemostatic clip 200 in an early pressure.

If the pressure is performed by the clip pressing part 160, the hemostatic clip 200 are transformed into an approximate rhomboid shape.

If the pressure is performed more in the above state, the upper and lower part of the hemostatic clip 200 is transformed into a side-by-side shape, therefore, it may be found that the clipping operation regarding the bleeding portion is performed.

Of course, the hemostatic clip 200 may have other shapes to clip well through the clip pressing part 160, however, it may need to have a shape that can occlude partially as described.

As described above, according to the present disclosure, it may be found that it is composed of a primary performing on the bleeding portion using holding type pincers, then clipping around the bleeding portion in order to perform hemostatic safely as the elementary technical gist.

As the above, it is explained referring to exemplary embodiments of the present disclosure, therefore, this is just an exemplary descriptions, accordingly, it may be found clearly in other exemplary descriptions such as various transformation, alteration, and equivalent other exemplary embodiments of the present disclosure without getting out of the gist and range of the present disclosure.

Therefore, true technical protecting range of the present disclosure may be determined according to content of attached claims.

INDUSTRIAL APPLICABILITY

The present invention can be applied to a variety of medical operations which can find the bleeding portion on the blood vessels that can occur in case of amputation of blood vessels or mistakes or accidents and perform hemostasis.

What is claimed is:

1. A closed loop-type hemostatic clipping device comprising,
 a first trigger and a second trigger on a body;
 holding type pincers connected with the first trigger, the holding type pincers are configured to hold a bleeding portion according to control of the first trigger;
 a clip holding part connected with the second trigger, the clip holding part moves to the bleeding portion according to control of the second trigger;
 a clip pressing part that in operation presses the clip holding part; and
 a hemostatic clip contained in the clip holding part, the hemostatic clip having built-in inner pincers, the hemostatic clip clips the bleeding part with the built-in inner pincers according to the clip pressing part operation,
 wherein the clip holding part is composed of an upper and a lower clip holding part, a prevention sill being formed at a front of each of the upper and the lower clip holding part, and the prevention sill preventing separation of the hemostatic clip from the clip holding part,
wherein the hemostatic clip has a square bracket shape in a plan view and an U-shape in a side view and the hemostatic clip has a closed loop-type shape having a proximally facing opening formed at a center.

2. The closed loop-type hemostatic clipping device of claim 1,
 wherein the clip holding part and the clip pressing part move together during an initial stage of the second trigger, and the clip pressing part moves only when the clip holding part reaches the location of the holding type pincers.

3. The closed loop-type hemostatic clipping device of claim 1,
 wherein a width of the hemostatic clip opening is formed more widely than a width of the holding type pincers.

* * * * *